(12) United States Patent
Legarda Ibañez

(10) Patent No.: US 7,348,321 B2
(45) Date of Patent: Mar. 25, 2008

(54) FLUMAZENIL FOR THE TREATMENT OF ALCOHOL DEPENDENCY

(75) Inventor: Juan Jose Legarda Ibañez, Madrid (ES)

(73) Assignee: Hythiam, Inc., Los Angeles, CA (US)

( * ) Notice: Subject to any disclaimer, the term of this patent is extended or adjusted under 35 U.S.C. 154(b) by 509 days.

(21) Appl. No.: 10/621,229

(22) Filed: Jul. 15, 2003

(65) Prior Publication Data

US 2004/0092509 A1    May 13, 2004

(51) Int. Cl.
    A61K 31/55    (2006.01)
(52) U.S. Cl. .................. 514/218; 514/220
(58) Field of Classification Search .......... 514/218, 514/220
    See application file for complete search history.

(56) References Cited

U.S. PATENT DOCUMENTS

| | | | |
|---|---|---|---|
| 5,434,156 A * | 7/1995 | Bjork et al. ............ | 514/255.01 |
| 5,519,017 A * | 5/1996 | Opitz ...................... | 514/215 |
| 6,455,276 B1 | 9/2002 | Le Bourdelles et al. | |
| 6,740,677 B2 | 5/2004 | Xue et al. | |

OTHER PUBLICATIONS

Aguirre et al. Plasma-b-endorphin levels in chronic alcoholics, Alcohol, vol. 7, pp. 409-412, 1990.*
Soderpalm et al. Benzodiazepines enhance the consumption and palatability of alcohol in the rat. Psychopharmacology, 1998, 137:215-222.*
American Psychiatric Association: Diagnostic and Statistical Manual of Mental Disorders, Fourth Edition, Washington, D.C., American Psychiatric Association, 1994, pp. 194-204.
Buck, K. J., Reversal of Alcohol Dependence and Tolerance by a Single Adminstration of Flumazenil, The Journal of Pharmacology and Experimental Therapeutics, 1991, vol. 257, No. 3, pp. 984-989.
File, S.E., Effects of Nitrendipine, Chlordiazepoxide, Flumazenil and Baclofen on the Increased Anxiety Resulting from Alcohol Withdrawal, Prog. Neuro-Psychopharmacol & Biol. Psychiatry, 1992, vol. 16, No. 1, pp. 87-93.
Gerra, G., Effectiveness of Flumazenil in the Treatment of Ethanol Withdrawal, Current Therapeutic Research, Jul. 1991, vol. 50, No. 1, pp. 62-66.
Nutt, D., Benzodiazepine Receptors in Alcohol Withdrawal Neuroschycopharmacology, May 1994, vol. 10, No. 35. Part 1.
Nutt, D., Flumazenil in Alcohol Withdrawal, Alcohol & Alcoholism, 1991, Suppl. 2, pp. 337-341.
Potokar, J. Flumazenil in Alcohol Withdrawal: a Double-blind Placebo-controlled Study. Alcohol & Alcoholism, 1997, vol. 32, No. 5, pp. 605-611.
Practice Management Information Corporation: International Classification of Diseases, 9th Revision, Clinical Modification, Sixth Edition (ICD-9-CM), 2004, selected pages.
Bell, E.C., et al., "Response to Flumazenil in the Late Luteal Phase and Follicular Phase of the Menstrual Cycle in Healthy Control Females," Psychopharmacology, vol. 172, pp. 248-254 (2004).
Berezhnoy, D., et al., "Conformational Changes at Benzodiazepine Binding Sites of $GABA_A$ Receptors Detected With a Novel Technique," J. Neurochemistry, vol. 92, pp. 859-866 (2005).
Betz, C., et al., "Could a Common Biochemical Mechanism Underlie Addictions?," J. Clin. Pharm Ther., vol. 25, No. 1, pp. 11-20 (2000) (Abstract Only).
Biggio, G., et al., "Molecular Mechanisms of Tolerance to and Withdrawal of GABA(A) Receptor Modulators," Eur. Neuropsychopharmacol., vol. 13, No. 6, pp. 411-423 (2003).
Boehm, S.L., et al., "γ-Aminobutyric Acid A Receptor Subunit Mutant Mice : New Perspectives on Alcohol Actions," Biochemical Pharmacology, vol 68, pp. 1581-1602 (2004).
Buckley, S.T., et al., "$GABA_A$ Receptor β Subunit mRNA Expression in the Human Alcoholic Brain," Neurochemistry International, vol. 45, pp. 1011-1020 (2004).
Casasola, C., et al., "Hyperexcitability Induced by GABA Withdrawal Facilitates Hippocampal Long-term Potentiation," Neuroscience, vol. 126, pp. 163-171 (2004).
Clark, M., Sensitivity of the Rat Hippocampal $GABA_A$ Receptor α4 Subunit to Electroshock Seizures, Neuroscience Letters, vol. 250, pp. 17-20 (1998).
Criswell, H.E., et al., "Effect of Zolpidem on Gamma-aminobutyric Acid (GABA)- Induced Inhibition Predicts the Interaction of Ethanol with GABA on Individual Neurons in Several Rat Brain Regions" J. Pharmacol. Exp. Therap., vol. 273, No. 1, pp. 526-536 (1995) (Abstract Only).
Davies, M., The Role of $GABA_A$ Receptors in Mediating the Effects of Alcohol in the Central Nervous System, J. Psychiatry Neurosci., vol. 28, No. 4, pp. 263-274 (2003).
Devaud L. L, et al., "Bidirectional Alterations of GABA(A) Receptor Subunit Peptide Levels in Rat Cortex During Chronic Ethanol Consumption and Withdrawal," J. Neurochem., vol. 69, No. 1, pp. 126-130 (1997), Abstract only.
Devaud L.L, et al., "Chronic Ethanol Consumption Differentially Alters the Express of Gamma-aminobutyric $acid_A$ . . . Chain Reaction Analysis," Mol. Pharmacol., vol. 48, No. 5, pp. 861-868 (1995), Abstract only.
Devaud L.L, et al., "Influence of Gender on Chronic Ethanol-Induced Alterations in $GABA_A$ Receptors in Rats," Brain Res., vol. 796, Nos. 1&2, pp. 222-230 (1998), Abstract only.
Devaud L.L, et al., "Sensitization of Gamma-Aminobutyric $acid_A$ Receptors to Neuroactive Steroids in Rats During Ethanol Withdrawal," J. Pharmacol. Exp. Ther., vol. 278, No. 2, pp. 510-517 (1996), Abstract only.
DuBois, D.W., et al., "Binge Ethanol Exposure Delays Development of GABAergic Miniature Postsynaptic Currents in Septal Neurons," Developmental Brain Research, vol. 152, pp. 199-212 (2004).

(Continued)

Primary Examiner—Jennifer Kim
(74) Attorney, Agent, or Firm—Kilpatrick Stockton LLP

(57) ABSTRACT

The invention relates to the use of flumazenil in developing a drug used for the sequential administration of small quantities of flumazenil at short intervals, until a therapeutically effective quantity is administered to treat alcohol dependence.

11 Claims, No Drawings

OTHER PUBLICATIONS

File, S.E., et al, "Effects of Nitrendipine, Chlordiazepoxide, Flumazeil and Baclofen on the Increased Anxiety Resulting from Alcohol Withdrawal," *Prog. Neuropsychopharmacol. Biol. Psychiatry*, vol. 16, No. 1, pp. 87-93 (1992) (Abstract Only).

File, S.E., et al., "Benzodiazepine Withdrawal: Behavioural Pharmacology and Neurochemical Changes." *Biochem. Soc. Symp.*, vol. 59, pp. 97-106 (1993) (Abstract Only).

File, S.E., et al., "Flumazenil but not Nitrendipine Reverses the Increased Anxiety During Ethanol Withdrawal in the Rat," *Psychopharmacology*, vol. 98, No. 2, pp. 262-264 (1989), Abstract only.

Finn, D.A., et al., "Differential Change in Neuroactive Steroid Sensitivity During Ethanol Withdrawal," *J. Pharmacology and Experimental Therapeutics*, vol. 292, No. 1, pp. 394-405 (2000).

Follesa, P., et al., Modulation of $GABA_A$ receptor Gene Expression by Allogpregnanolone and Ethanol, *Euro. J. Phamacology*, vol. 500, pp. 413-425 (2004).

Follesa, P., et al., γ-Hydroxybutyric Acid and Diazepam Antagonize a Rapid Increase in $GABA_A$ Receptors α4 Subunit mRNA Abundance Induced by Ethanol Withdrawal in Cerebellar Granule Cells, *Molecular Pharmacology*, vol. 63, No. 4, pp. 896-907 (2003).

Green, K.L, et al., The Influence of Menstrual Cycle Phase on Sensitivity to Ethanol-Like Discriminative Stimulus Effects of $GABA_A$-Positive Modulators, *Pharmacology Biochemisty and Behavior*, vol. 64, No. 2, pp. 379-383 (1999).

Grobin, A.C., et al., "The role of GABA(A) Receptors in the Acute and Chronic Effects of Ethanol," *Psychopharmacology* (Berl.), vol. 139, Nos. 1-2, pp. 2-19 (1998) (Abstract Only).

Grobin, A.C., et al., "Chronic Ethanol Administration Alters Immunoreactivity for $GABA_A$ Receptor Subunits in Rat Cortex in a Region-Specific Manner," *Alcholosim*, vol. 24, No. 8, pp. 1137-1144 (2000), Abstract only.

Hanchar, H.J., et al, "Alcohol Effects on γ-aminobutyric Acid Type A Receptors: Are Extrasynaptic Receptors the Answer?," *Life Sciences*, vol. 76, pp. 1-8 (2004).

Hirani, K., et al., "Evaluation of GABAergic Neuroactive Steroid 3alpha-hydroxy-5alpha-pregnane-20-one as a Neurobiological Substrate for the Anti-Anxiety Effect of Ethanol in Rats," *Psychopharmacology* (Berl.), (Epub ahead of print) (2005) (Abstract Only).

Holtman, Jr., J.R., et al., "Modification of Morphine Analgesia and Tolerance by Flumazenil in Male and Female Rats," *Euro. J. Pharmacology*, vol. 470, pp. 149-156 (2003).

Janak, P.H., et al., "The Reinforcing Effects of Ethanol are Altered by the Endogenous Neurosteroid, Allpregnanolone," *Alcohol Clin. Exp. Res.*, vol. 22, No. 5, pp. 1106-1112 (1998) (Abstract Only).

Janis, G.C., et al., Effects of Chronic Ethanol Consumption and Withdrawal on the Neuroactive Steroid 3alpha-hydroxy-5alpha-pregnan-20-one in Male and Female Rats, *Alcohol Clin. Exp. Res.*, vol. 22, No. 9, pp. 2055-2061 (1998) (Abstract Only).

June, H.L., et al., "Ethanol Self-Administration in Freely Feeding and Drinking Rats; Effects of Ro15-4513 alone, and in Combination with Ro15-1788 (Flumazenil)," *Psychopharmacology* (Berl.), vol. 115, No. 3, pp. 332-339 (1994) (Abstract Only).

Kang, M., et al., "Persistent Reduction of GABA(A) Receptor-Mediated Inhibition in Rat Hipposcampus After Chronic Intermittent Ethanol Treatment," *Brain Res.*, vol. 709, No. 2, p. 221-228 (1996) (Abstract Only).

Kang, M., et al., "Alteration in the Sensitivity of GABA(A) Receptors to Allosteric Modulatory Drugs in Rat Hippocampus After Chronic Intermittent Ethanol Treatment," *Alcohol Clin. Exp. Res.*, vol. 22, No. 9, p. 2165-2173 (1998) (Abstract Only).

Knapp, D.J., et al., "SB242084, Flumazenil, and CRA1000 Block Ethanol Withdrawal-Induced Anxiety in Rats," *Alcohol*, vol. 32, pp. 101-111 (2004).

Ma, L., et al., "Transcriptional Regulation of the Mouse Gene Encoding the α-4 Subunit of the $GABA_A$ Receptor," *J. Biological Chemistry*, vol. 279, No. 39 pp. 40451-40461 (2004).

Mahmoudi, M.K., et al., "Chronic Intermittent Ethanol Treatment In Rats Increases GABA (A) Receptor Alpha4-subunit Expression: Possible Relevance to Alcohol Dependence," *J. Neurochem.*, vol. 68, No. 6, pp. 2485-2492 (1997) (Abstract Only).

Mann, K., "Pharmacotherapy of Alcohol Dependence," *CNS Drugs*, vol. 18, No. 8, pp. 485-504 (2004).

Matthews, D.B., et al., "Differential Regulation of GABA(A) Receptor Gene Expression by Ethanol in the Rat Hippocampus Versus Cerebral Cortex," *J. Neurochem.*, vol. 70, No. 3, pp. 1160-1166 (1998) (Abstract Only).

Mitsuyama, H., et al., "GABA(A) Receptor Alpha1, Alpha4, and Beta3 Subunit mRNA and Protein Expression in the Frontal Cortex of Human Alcoholics," *Alcohol Clin. Exp. Res.*, vol. 22, No. 4, pp. 815-822 (1998) (Abstract Only).

Moy, S.S. et al., "Enhanced Ultrasonic Vocalization and Fos Protein Expression Following Ethanol Withdrawal: Effects of Flumazenil," *Psychopharmacology*, vol. 152, pp. 208-215 (2000).

Moy, S.S., et al., "Flumazenil Blockade of Anxiety Following Ethanol Withdrawal in Rats," *Psychopharmacology*, vol. 131, pp. 354-360 (1997).

Potokar, J., et al., "Flumazenil in Alcohol Withdrawal: A Double-Blind Placebocontrolled Study," *Alcohol*, vol. 32, No. 5, pp. 605-611 (1997), Abstract only.

Sanna, E., et al., "Changes in $GABA_A$ Receptor Gene Expression Associated with Selective Alterations in Receptor Function and Pharmacology After Ethanol Withdrawal," *J. of Neuroscience*, vol. 23, No. 37, pp. 11711-11724 (2003).

Savic, I., et al., "Feasibility of Reversing Benzodiazepine Tolerance with Flumazenil," *Lancet*, vol. 337, pp. 133-137 (1991).

Schmitt, U., et al., "Free-choice Ethanol Consumption Under the Influence of GABAergic Drugs in Rats," *Alcohol Clin. Exp. Res.*, vol. 26, No. 4, pp. 457-462 (2002) (Abstract Only).

Stanley, K.M., et al., "Impact of an Alcohol Withdrawal Syndrome Practice Guideline on Surgical Patient Outcomes," *Pharmacotherapy*, vol. 23, No. 7, pp. 843-854 (2003) (Abstract Only).

Sundstrom-Poromaa, I., et al., "Hormonally Regulated $α_4β_2δ$ $GABA_A$ Receptors are a Target for Alcohol," *Nature Neuroscience*, vol. 5, No. 8, pp. 721-722 (2002).

Uzbay, I.T., et al., "Effects of Flumazenil on Ethanol Withdrawal Syndrome in Rats," *Arzneimittelforschung*, vol. 45, No. 2, pp. 120-124 (1995) (Abstract Only).

Vanover, K.E., et al., "Positive Allosteric Modulators of the $GABA_A$ Receptor: Differential Interaction of Benzodiazepines and Neuroactive Steroids With Ethanol," *Psychopharmacology*, vol. 141, pp. 77-82 (1999).

Vanover, K.E., "Effects of Benzodiazepine Receptor Ligands and Ethanol in Rats Trained to Discriminate Pregnanolone," *Pharmacology, Biochemistry and Behavior*, vol. 67, pp. 483-487 (2000).

Verheul, R., et al., "A Three-Pathway Psychobiological Model for Craving for Alcohol," *Alcohol & Alcoholism*, vol. 34, No. 2, pp. 197-222 (1999).

Weinbroum, A.., et al., "Flumazenil Potentiation of Postoperative Morphine Analgesia," *Clin. J. Pain*, vol. 16, No. 3, pp. 193-199 (2000) (Abstract Only).

White, J., et al., "Antagonism of a Nicotine Plus Midzaolam Discriminative Cue in Rats," *Behav. Pharmacol.*, vol. 5, No. 3, pp. 351-355 (1994) (Abstract Only).

Van Miert, AS, "Appetite-Modulating Drugs in Dwarf Goats, With Special Emphasis on Benzodiazepine-Induced Hyperphagia and its Antagonism by Flumazenil and RO 15-3505", *J. Vet Pharmacol Ther.*, Jun; 12(2):147-56 (1989), Abstract only.

Zheng, T.M., et al., "Chronic Flumazenil Alters GABA(A) Receptor Subunit mRNA Expression, Translation Product Assembly and Channel Function in Neuronal Cultures," *J. Pharmacol. Exp. Ther.*, vol. 277, No. 1, pp. 525-533 (1996) (Abstract Only).

Baldwin, H.A., et al., "Flumazenil Prevents the Development of Chlordiazepoxide Withdrawal in Rats Tested in the Social Interaction Test of Anxiety," *Psychopharmacology*, vol. 97, No. 3, pp. 424-426 (1989), Abstract Only.

Brooks-Kayal-A.R., et al., "Human Neuronal α-Aminobutyric $Acid_A$ Receptors : Coordinated Subunit mRNA Expression and Functional Correlates in Individual Dentate Granule Cells," *J. Neuroscience*, vol. 19, No. 19, pp. 8312-8318 (1999).

Ferrar, G., et al., "Increased Expression of the Neuropeptide α receptor α1 Gene in the Medical Amygdala of Transgenic Mice Induced by Long-term Treatment with Progesterone or Alloprenanolone," *J. Neurochemistry*, vol. 79, pp. 417-425 (2001).

Frostholm, A., et al., "Harmaline-induced Changes in Gamma Aminobutyric Acid$_A$ Receptor Subunit mRNA Expression in Murine Olivocerebellar Nuclei," *Molecular Brain Research*, vol. 85, pp. 200-208 (2000).

Gee, KW et al., "A Putative Receptor for Neurosteroids on the GABAA Receptor Complex: the Pharmacological Properties and Therapeutic Potential of Epalons", *Crit Rev Neurobiol.* 1995;9(2-3):207-27 (Abstract Only).

Gulinello, M., et al., "Progesterone Withdrawal Increases the α4 Subunit of the GABA$_A$ Receptor in Male Rats in Association With Anxiety and Altered Pharmacology—A Comparison With Female Rats," *Neuropharmacology*, vol. 43, pp. 701-714 (2000).

Gulinello, M., et al., "Anxiogenic Effects of Neurosteriod Exposure: Sex Differences and Altered GABA$_A$ Receptor Pharmacology in Adult Rats," *J. Pharmacology and Experimental Therapeutics*, vol. 305, No. 2, pp. 541-548 (2003).

Hawkinson, J.E., "Substituted 3β-Phenylethynyl Derivatives of 3α-Hydroxy-5α-pregnan-20-one: Remarkably Potent Neuroactive Steroid Modulators of γ-Aminobutyric Acid$_A$ Receptors," *J. Pharmacology and Experimental Therapeutics*, vol. 287, No. 1, p. 198-207 (1998).

Hogenkamp, D.J., et al., "Synthesis and in Vitro Activity of 3β-Substituted-3β-Hydroxypregnan-20-ones: Allosteric Modulators of the GABA$_A$ Receptor," *J. Med. Chem.*, vol. 40, pp. 61-72 (1996).

Hsu, F. et al., "Progesterone Withdrawal Reduces Paired-Pulse Inhibition in Rate Hippocuampus: Dependence on GABAA Receptor β4 Subunit Upregulation," *J. Neurophysiol.*, vol. 89, pp. 186-198 (2003).

Krogsgaard-Larsen, P., et al., "GABA$_A$ Agonists and Partial Agonists: THIP (Gaboxadol) as a Non-Opoid Analgesic and a Novel Type of Hypnotic," *Biochemical Pharmacology*, vol. 68, pp. 1573-1580 (2004).

Holt, R.A., et al., "Chronic Treatment with Diazepam or Abecarnil Differently Affects the Expression of GABA$_A$ Receptor Subunit mRNAs in the Rat Cortex," *Neuropharmacology*, vol. 35, Nos. 9 & 10, pp. 1457-1463 (1996), Abstract only.

Lan, N.C., et al., "Differential Responses of Expressed Recombinant Human Gamma-aminobutyric acidA Receptors to Neurosteroids," *J. Neurochem.*, vol. 57, No. 5, pp. 1818-1821 (1991) (Abstract Only).

Lee, C., et al., "Effects of Benzodiazepine Receptor Antagoinst, Flumazenil, on Antinociceptive and Behavioural Responses to the Elevated Plusmaze in Mice," *Neuropharmacology*, vol. 30, No. 12A, pp. 1263-1267 (1991) (Abstract Only).

Medina, J.H., et al., "Overview-Flavonoids: A New Family of Benzodiazepine Receptor Ligands," *Neurochemical Research*, vol. 22, No. 4, pp. 419-425 (1997).

Smith, S.S., et al., "Neurosteroid Administration and Withdrawal Alter GABA$_A$ Receptor Kinetics in CA1 Hippocamppus of Female Rats," *J. Physiol.*, vol. 567, Pt. 2, pp. 421-436 (2005) (Abstract Only).

Sur, C., et al., "Preferential Coassembly of β4 and δ Subunits of the γ-Aminobutyric AcidA Receptor in Rat Thalamus" *American Society of Pharmacology and Experimental Therapeutics*, vol. 56, pp. 110-115 (1998).

Whittemore, E.R., et al., "Pharmacology of the Human Gamma-Aminobutyric acidA Receptor Alpha 4 Subunit Expressed in *Xenopus Laevis* Oocytes," *Mol. Pharmacol.*, vol. 50, No. 5, pp. 1364-1375 (1996) (Abstract Only).

Wisden, W., et al., "Cloning, Pharmacological Characteristics and Expression Pattern of the Rat GABA$_A$ Receptor Alpha 4 Subunit," *FEBS Lett.*, vol. 289, No. 2, pp. 227-230 (1991) (Abstract Only).

Adkins, C.E., et al., "α$_4$β$_3$δ GABA$_A$ Receptors Characterized by Fluorescence Resonance Energy Transfer-derived Measurements of Membrane Potential," *J. Biological Chemistry*, vol. 276, No. 42, pp. 38934-38939 (2001).

Akk, G., et al., "Activation of GABA(A) Receptors Containing the alpha4 subunit by GABA and Pentobarbital," *J. Physiol.*, vol. 556, Part 2, , (2004), p. 387-399.

Banerjee, P.K., et al., "Alterations in GABA$_A$ Receptor β1 and β4 Subunit mRNA Levels in Thalamic Relay Nuclei Following Absence-like Seizures in Rats," *Experimental Neurology*, vol. 154, pp. 213-223 (1998).

Biggio, G., et al., "GABA$_A$-receptor Plasticity During Long-Term Exposure to and Withdrawal from Progesterone," *Int. Rev. Neurobiol.*, vol. 46, pp. 207-241 (2001), Abstract only.

Burt, D.R., "Alpha Subunit Position and GABA Receptor Function," *Science's STKE*, No. 270, PE5, pp. 1-2 (2005).

Lovick, T.A., et al., "Changes in GABA$_A$ Receptor Subunit Expression in the Midbrain During the Oestrous Cycle in Wistar Rats," *Neuroscience*, vol. 131, pp. 397-405 (2005).

Lujan, R., et al., "Glutamate and GABA Receptor Signalling in the Developing Brain," *Neuroscience*, vol. 130, pp. 567-580 (2005).

Mody, I., "Distinguishing between GABA$_A$ Receptors Responsible for Tonic and Phasic Conductances," *Neurochemical Research*, vol. 26, Nos. 8-9, pp. 907-913 (2001).

Porter, B.E., et al., "Heterogenous GABA(A) Receptor Subunit Expression in Pediatric Epilepsy Patients," *Neurobiol. Dis.*, vol. 18, No. 3, pp. 484-491 (2005) (Abstract Only).

Quirk, G.J., et al., "Inhibition of the Amygdala: Key to Pathological States?," *Ann. N.Y. Acad. Sci.*, vol. 985, pp. 263-272 (2003).

Rissman, R.A., et al., "Subregional Analysis of GABA$_A$ Receptor Subunit mRNAs in the Hippocampus of Older Persons with and without Cognitive Impairment," *J. of Chemical Neuroanatomy*, vol. 28, pp. 17-25 (2004).

Saitoh, K., et al., "Nigral GABAergic Inhibition Upon Mesencephalic Dopaminergic Cell Groups in Rats," *Eur. J. Neurosci.*, vol. 19, No. 9, pp. 2399-2409 (2004) (Abstract Only).

Sedvall, G., et al., "Recent Advances in Psychiatric Brain Imaging," *Acta Radiol.Suppl.*, vol. 374, pp. 113-115 (1990) (Abstract Only).

Smith, S.S., et al., "GABA$_A$ Receptor β4 Subunit Suppression Prevents Withdrawal Properties of an Endogenous Steroid," *Nature*, vol. 392, pp. 926-930 (1998).

Yang, W., "Cloning and Characterization of the Human GABA$_A$ Receptor Alpha 4 Subunit: Identification of a Unique Diazepam-Insensitive Binding Site," *Eur. J. Pharmacol.*, vol. 291, No. 3, pp. 319-325 (1995) (Abstract Only).

Zheng, T.M., et al., "Changes in γ-aminobutyrate Type A Receptor Subunit mRNAs, Translation Product Expression, and Receptor Function During Neuronal Maturation in vitro," *Proc. Natl. Acad. Sci. USA*, vol. 91, pp. 10952-10956 (1994).

Smith, A.J., et al., "Effect of α Subunit on Allosteric Modulation of Ion Channel Function in Stably Expressed Human Recombinant γAminobutyric AcidA Receptors Determined Using $^{36}$Cl Ion Flux," *Molecular Pharmacology*, vol. 59, No. 5, pp. 1108-1118 (2001).

Klotz, U. et al., "Pharmacokinetics and Clinical Use of Flumazenil," *Clinical Pharmacokinetics*, 14(1), pp. 1-12 (1988).

"Encyclopedia of Medicaments", Moscow, RLC 2000, pp. 988-989 (English translation of Russian provided).

"The Merck Manual", M, MIR Publishers, v.2, p. 23 (1997) (English translation of Russian provided).

* cited by examiner

FLUMAZENIL FOR THE TREATMENT OF ALCOHOL DEPENDENCY

FIELD OF THE INVENTION

The invention relates to the use of pharmaceutical compositions that contain flumazenil in the treatment of alcohol dependency, more specifically to improvements in the use of flumazenil in the treatment of said dependency.

BACKGROUND OF THE INVENTION

Alcohol dependency is a syndrome that develops in alcoholics who, all at once, stop consuming alcohol. Minor symptoms include tremor, weakness, sweats, and nausea. The most severe cases include convulsions and hallucinations. If untreated, alcohol withdrawal may cause delirium tremens.

The customary treatment of alcohol dependency includes the administration of vitamin B and C complexes, benzodiazepines (to calm agitation and to help prevent dependency), and, sometimes, disulfiram (to prevent alcohol use). A review of the various pharmacological treatments existing for the treatment of alcohol dependency can be found in A Practice Guideline for the Treatment of Patients With Substance Use Disorders: Alcohol, Cocaine and Opioids, produced by the Work Group on Substance Use Disorders of the American Psychiatric Association and published in Am. J. Psychiatry 152:11, November 1995 Supplement. An updated review of the treatment of alcohol dependency was made by Mayo-Smith et al., JAMA Jul. 9, 1997, Vol. 278, No. 2, who conclude by indicating that the benzodiazepines (alprazolam, diazepam, halazepam, lorazepam or oxazepam) are agents suitable for the treatment of alcohol dependency, whereas β-blockers (propranolol), neuroleptics (chlorpromazine and promazine), clonidine and carbamazepine, may be used in coadjuvant therapy, but their use is not recommended as a monotherapy. In, none of the reviews mentioned is the use of flumazenil considered in the treatment of the alcohol withdrawal syndrome.

Flumazenil [ethyl 8-fluoro-5,6-dihydro-5-methyl-6-oxo-4H-imidazol[1,5-a][1,4]benzodiazepine-3-carboxylate] is a benzodiazepine antagonist which selectively blocks the effects exerted on the central nervous system via the benzodiazepine receptors. This active principle is indicated to neutralize the central sedative effect of the benzodiazepines; consequently, it is regularly used in anesthesia to end the general anesthesia induced and maintained with benzodiazepines in hospitalized patients, or to stop the sedation produced with benzodiazepines in patients undergoing brief diagnostic or therapeutic procedures on an inpatient or outpatient basis.

Some clinical studies have examined the role of flumazenil in the reversal of alcohol withdrawal syndrome.

Gerra et al., 1991, Current Therapeutic Research, Vol. 50, 1, pp 62-66, describe the administration to 11 selected alcoholics (who did not have cirrhosis, metabolic disorders, convulsions, addictions to other substances or psychiatric disorders) of 2 mg/day of flumazenil divided into 4 doses (0.5 mg), intravenously (IV), in saline solution, every 6 hours for 48 hours, continuing the treatment with flumazenil for 2 more days. The use of 0.5 mg of flumazenil is based on the presentation of pharmaceutical preparations that contain said active principle, for example ANEXATE7 [sic] ROCHE, but not on studies performed in humans concerning the level of occupation of the receptors involved. Taking into consideration the fact that the half-life of flumazenil in the human body is approximately 45 minutes, the administration of 0.5 mg of flumazenil every 6 hours (i.e., 0.08 mg/hour of flumazenil) does not seem adequate to effectively cover the cerebral benzodiazepine receptors (Savic et al., Lancet, 1991, 337, 133-137), which confirms what was stated by Gerra et al., loc. cit., who, on page 64, next to last paragraph, state that they did not observe significant changes in either the blood pressure or in the heart rate of the patients after the administration of flumazenil, which is surprising when there had been an effective interaction of the fumazenil administered with the cerebral benzodiazepine receptors. The tests performed by Gerra et al. present some characteristics that are far from the actual circumstances, for example, the tests were performed on a small sample (11 individuals) of select patients not representative of the pathology considered since it is relatively customary that these patients have cirrhosis, metabolic disorders, convulsions, addictions to other substances (cocaine, heroin, etc.) and/or psychiatric disorders. Moreover, Gerra et al. do not present data concerning the evaluation of the dependency either before or after administration of the drug. The treatment with flumazenil, in accordance with the protocol developed by Gerra et al., lasts 4 days, which means a very long period of time which causes inconvenience for the patient as well as an increase in the cost and duration of the treatment.

Nutt et al. [Alcohol & Alcoholism, 1993, Suppl. 2, pp 337-341. Pergamon Press Ltd.; Neuropschychopharmacology, 1994, Vol. 10, 35, part 1, Suppl., p. 85f) describe the administration to 8 alcoholics in the acute withdrawal phase of 2 mg of flumazenil, by IV, for 1 minute. This dosage was selected on the basis of studies that demonstrated that with said dose approximately 75% of the cerebral benzodiazepine receptors are occupied (Savic et al., Lancet, 1991, 337, 133-137). The results obtained after the administration of flumazenil were not completely satisfactory since in some cases, there was an immediate worsening of the withdrawal symptoms, especially of sweats and anxiety. In other cases, the withdrawal symptoms disappeared but returned a few hours later. Since flumazenil is metabolized and eliminated very quickly, the IV administration of a relatively high quantity of flumazenil in a single dose of 2 mg, for 1 minute, has several disadvantages since, on the one hand, it triggers side effects, and, on the other, some of the flumazenil administered yields no pharmacological response or a weak response which means an unacceptable expense.

The tests performed by Gerra et al. and by Nutt et al., loc. cit., with flumazenil to treat alcohol dependency do not provide representative results due to the use of a very small sample (only 19 patients tested of the approximately 600,000 patients treated annually in the United States during the years 1991-1994, years during which the work of Gerra et al. and of Nutt et al. occurred) which is not representative of said patients (the 11 patients treated in the trial of Gerra et al. were selected alcoholics who did not have cirrhosis, metabolic disorders, convulsions, addictions to other substances or psychiatric disorders). Moreover, the results obtained are not conclusive since in some cases, no significant changes were observed in either the blood pressure or the heart rate of patients after the administration of flumazenil (Gerra et al., loc. cit.); whereas, in other cases, an immediate worsening of the withdrawal symptoms was observed, especially sweats and anxiety (Nutt et al., loc. cit.). These very discouraging results seem to have favored the abandonment of flumazenil as a therapeutic agent for the treatment of alcohol dependency, a situation which could explain the absence of publications of new trials associated with the treatment of alcohol dependency with flumazenil during the past 6 years as well as the failure to include said treatment in the aforementioned reviews concerning the treatment of alcohol dependency [A Practice Guideline for the Treatment of Patients With Substance Use Disorders: Alcohol, Cocaine and Opioids and Mayo-Smith et al.].

Consequently, it would be desirable to be able to determine without ambiguity whether flumazenil may be a suitable agent to treat alcohol dependency and, if so, to develop a protocol for administration of flumazenil for the treatment of alcohol dependency that would enable effectively eradicating the symptoms of alcohol withdrawal. It would also be desirable to reduce the quantity of flumazenil to be administered per dose during a short period of time for the purpose of reducing, on the one hand, the risk of undesirable side effects, and, on the other, to reduce or avoid unnecessary and pointless consumption of flumazenil.

BRIEF DESCRIPTION OF THE INVENTION

The invention deals with the problem of developing a new method for the treatment of alcohol dependency based on safe and effective administration of flumazenil and which requires a short period of time to effectively eradicate the symptoms of alcohol dependency.

The solution provided by this invention is based on the use of pharmaceutical compositions that contain a therapeutically effective quantity of flumazenil for the treatment of alcohol dependency and the eradication of the symptoms of said syndrome in a short period of time, with said pharmaceutical compositions containing small quantities of flumazenil and being intended for sequential administration.

Thus, one object of this invention consists in a method for the effective administration of flumazenil that uses a smaller quantity of drug per dose unit to be administered, by sequential administration of small quantities of flumazenil, to eradicate the symptoms of alcohol withdrawal in a short period of time, while simultaneously reducing the side effects caused by the administration of large quantities of the drug in a single application in a short period of time.

Another object of this invention consists in a method for the administration of flumazenil by sequential administration of small doses of flumazenil, without compromising its effects of eradication of the symptoms of alcohol withdrawal, effectively and reproducibly, in a short period of time.

Another additional object of this invention consists in the use of flumazenil to produce a drug for sequential administration, at short time intervals, of small quantities of flumazenil, until a therapeutically effective quantity to treat alcohol dependency has been administered.

Another additional object of this invention consists in a method for the treatment of alcohol dependency that includes administration, to a patient in need of said treatment, of a therapeutically effective quantity of flumazenil, broken down into small quantities of flumazenil and intended for sequential administration, at short time intervals, until said therapeutically effective quantity to treat alcohol dependency has been reached.

DETAILED DESCRIPTION OF THE INVENTION

The invention relates to the use of flumazenil to produce a drug for sequential administration, at short time intervals, of small quantities of flumazenil, until a therapeutically effective quantity to treat alcohol dependency has been administered.

More specifically, the invention relates to the use of flumazenil to produce a drug for sequential administration, at time intervals between 1 and 15 minutes, of quantities of flumazenil between 0.1 and 0.3 mg, until a therapeutically effective quantity, usually between 1.5 and 2.5 mg/day, of flumazenil has been administered, to treat alcohol dependency.

In one embodiment, the invention relates to the use of flumazenil to produce a drug for sequential administration, at intervals of 3 minutes, of 0.2 mg of flumazenil, until a therapeutically effective quantity of 2 mg/day of flumazenil has been administered, to treat alcohol dependency.

In the meaning used in this description, the term drug includes the group of pharmaceutical compositions that contain flumazenil, along with the pharmaceutically acceptable excipients suitable for the form of administration of said pharmaceutical compositions.

Although the trials described in the prior art associated with the treatment of alcohol dependency with flumazenil include the administration to the patient of an IV perfusion of 2 mg/day of flumazenil divided into 4 doses (0.5 mg/dose), every 6 hours for 48 hours, or 2 Mg by IV for 1 minute, it was discovered, surprisingly, that flumazenil can be safely administered to said patients, in small quantities, applied sequentially and separated by a relatively short interval of time, until a therapeutically effective quantity of flumazenil to treat alcohol dependency has been reached.

This surprising discovery means that it is possible to administer flumazenil in smaller doses than was believed were necessary to obtain the desired therapeutic response, which reduces the risk of secondary effects in the patient (as a result of reducing the quantity of drug administered per dose applied), on the one hand, and, on the other, provides a better use of flumazenil to treat the symptoms of alcohol withdrawal and to reduce the unnecessary and pointless consumption of said drug (which increases convenience and the quality of life of the patient and reduces cost) to treat alcohol dependency in a very short period of time.

Example 1 demonstrates that the administration to patients of 2 mg/day of flumazenil divided into doses of 0.2 mg every 3 minutes eradicates the symptoms of alcohol withdrawal in a high percentage of the patients treated.

Consequently, in one embodiment, the invention relates to the use of flumazenil to produce a drug for administration, sequentially, of 0.2 mg of flumazenil every 3 minutes, up to a quantity of 2 mg/day, to treat alcohol dependency.

Flumazenil may be administered by any appropriate route of administration, for example, orally or parenterally, for which it will be formulated with the appropriate excipients for the form of administration to be used. In one embodiment, flumazenil is administered by IV.

The invention also relates to a method for the treatment of alcohol dependency that includes the administration to a patient in need of said treatment of a therapeutically effective quantity of flumazenil, usually between 1.5 and 2.5 mg/day of flumazenil, broken down into quantities of flumazenil between 0.2 and 0.3 mg and intended for sequential administration, at time intervals between 1 and 15 minutes, until said therapeutically effective quantity of flumazenil to treat alcohol dependency has been reached.

Flumazenil may be administered by any appropriate route of administration, for example, orally or parenterally, for which it will be formulated with the appropriate excipients for the form of administration to be used. In one embodiment, flumazenil is administered by IV.

The method for the treatment of alcohol dependency provided by this invention is applicable to any patient who, when the treatment is to begin, has no acute or uncompensated illness, or is not taking medication contraindicated with flumazenil. In general, the method of treatment of alcohol dependency provided by this invention begins with a complete medical and psychological examination. Before and after administration of flumazenil, the symptoms of alcohol withdrawal, heart rate, and blood pressure are evaluated. If the patient presents an anxiety crisis, it is possible to administer an appropriate therapeutic agent, for example, clomethiazole, before administration of flumazenil. Likewise, if the patient presents a severe diagnosis of benzodiazepine dependency, the first administration of flumazenil is carried out under sedation, for example, with propofol, under intensive care conditions. The administration of flumazenil may be carried out orally or intravenously, for example, by boluses that contain the appropriate quantity and under observation of the patient's reaction. Once inpatient treatment has concluded, as part of the therapeutic program, the patient must continue pharmacological treatment and continue sessions with his therapist to evaluate his progress. The treatment is supplemented by a semistructured follow-up of the cognitive behavior of the patient.

The following example demonstrates the invention and must not be considered to limit the scope thereof.

EXAMPLE 1

Treatment of Patients with Flumazenil Sequentially and at Low Dose 1.1 Experimental Protocol 64 alcoholics (51 males and 13 females) voluntarily entered a treatment program to discontinue the use of alcohol. Said patients were provided the appropriate information and the corresponding informed consent form was obtained from them. The patients were warned not to drink alcohol the morning on which the treatment was to be carried out to enable better evaluation of the withdrawal symptoms.

Table 1 summarizes the characteristics of the patients treated associated with alcohol use.

TABLE 1

| Characteristics of the patients associated with alcohol use | | | | |
|---|---|---|---|---|
| | Mean | SD | Minimum | Maximum |
| Age (years) | 42.7 | 10.2 | 20 | 75 |
| Age at the beginning of daily alcohol use (years) | 24.6 | 10.2 | 6 | 71 |
| Daily units of alcohol intake | 24.9 | 15.4 | 4 | 73 |
| γ-glutamyl transpeptidase (GGT) | 159.1 | 227.2 | 12 | 1.230 |
| Corpuscular volume (RBC) | 97.8 | 6.4 | 72 | 111 |
| Number of previous detoxifications | 1.6 | 1.2 | 0 | 5 |

[SD: Standard deviation]
NOTE:
85% consumed alcohol daily and 39.1% consumed benzodiazepines daily.

Before starting the treatment, the patients underwent a complete medical and psychological examination. The monitoring of the patients throughout the morning included a complete blood count, a biochemical profile [creatinine, glucose, urea, cholesterol (HDL and LDL), triglycerides, alkaline phosphatase, LDH (lactic dehydrogenase) and total proteins], hepatic function tests [GOT, GPT, GGT, bilirubin], electrocardiogram and, if need be, pregnancy test and x-ray examination. The exclusion criteria applied included acute or uncompensated illnesses, as well as the taking of any drug contraindicated with flumazenil. No patient was excluded after the pre-admission interview and the tests performed. Admission of one patient was postponed until his cardiac pathology was checked.

Before and after the administration of flumazenil, the withdrawal symptomatology was measured using the CIWA-A evaluation (Adinoff et al., Medical Toxicology 3:172-196 (1988)), as well as heart rate and blood pressure.

Table 2 presents the treatment protocol followed during hospitalization.

TABLE 2

| Protocol followed during hospitalization | | | |
|---|---|---|---|
| Time | Day of admission | Day 2 | Day of discharge |
| 9:00 a.m. | | Clomethiazole 192 mg<br>Vitamin B Complex<br>Piracetam 3 g (oral)<br>Drink with vitamins, minerals, proteins, and amino acids | Clomethiazole 192 mg<br>Vitamin B Complex<br>Piracetam 3 g (oral)<br>Drink with vitamins, minerals, proteins, and amino acids |
| 11:00 a.m. | | Flumazenil 2 mg | |
| 1:00 p.m. | Clomethiazole 192 mg<br>Vitamin B Complex<br>Piracetam 3 g (oral) | | |
| 4:30 p.m. | Flumazenil 2 mg | | |
| 7:30 p.m. | Vitamin B Complex | Vitamin B Complex<br>Disulfiram 250 mg | |
| 9:30 p.m. | Clomethiazole 384 mg | Clomethiazole 384 mg | |

Flumazenil was administered at a dose of 0.2 mg every 3 minutes (up to a total of 2 mg/day), because of the fact that the effects of flumazenil can be detected after 1-2 minutes after their administration. This quantity per dose was established to minimize the adverse side effects associated with withdrawal or interactions with other pharmaceuticals or psychopathologies. By administration of 2 mg of flumazenil per day, more than 55% of the GABA B receptors were occupied.

Patients who presented marked anxiety were administered an additional dose of 192 mg of clomethiazole 30 minutes before administration of flumazenil. In those patients who presented a severe diagnosis of benzodiazepine dependency, the initial administration of flumazenil was performed under sedation with propofol under intensive care conditions.

Before discharge from the hospital, the following medications were prescribed:
Vitamin B complex: 1 month 1-1-0 (breakfast-lunch-dinner);
Piracetam 3 g: 1 week 1-0-0; piracetam 800 mg: 1 month 1-1-0;
Fluoxetine 20 mg: 2 months 1-0-0;
Clomethiazole 192 mg: 1 week 1-0-1, and reduction to 0-0-0 during the second week; and
Disulfuram 250 mg 1-0-0.

As part of the treatment program, the patients were instructed to attend the outpatient treatment center for 9 months with decreasing frequency [once a week for the first three months, once every two weeks during the second three months, and once a month during the third three months].

Likewise, a semistructured follow-up of cognitive behavior was implemented. Individual and family psychotherapy was focused on 4 major interventions (cognitive restructuring, work therapy, prevention of relapse, and stress reduction) aimed at rehabilitating the social, family, work, personal and leisure life of the patient.

1.2 Results

Of the 64 patients treated, in 3 cases, the first administration of flumazenil was interrupted and postponed to the following day: one of them, who was obviously intoxicated with alcohol, demonstrated a distressing increase in confusion, another had a significant increase in distal tremors, and the other, who was also addicted to benzodiazepines, demonstrated a significant increase in anxiety. Another group of 3 patients received the first dose of flumazenil under sedation with propofol in the intensive care unit.

Approximately 10% of the patients suffered headache during or immediately following the administration of flumazenil, which disappeared after a few minutes, or after administration of metamizole magnesium.

Results After the First Administration of Flumazenil

The CIWA-A scoring of 55 patients showed that:
47.3% had a significant reduction (t: −7.713; p<0.000);
40.0% experienced no change; and
12.7% had a significant increase (t: 2.511; p<0.046) [in the three cases presenting the greatest increase, the treatment was discontinued].
The heart rate values of 55 patients showed that:
50.9% had a significant reduction (t: −8.820; p<0.000);
40.0% experienced no change; and
9.1% had a significant increase (t: 4.750; p<0.009).

The systolic blood pressure values of 53 patients showed that:
47.2% had a significant reduction (t: −9.908; p<0.000);
37.7% experienced no change; and
15.1% had a significant increase (t: 4.314; p<0.004).
The diastolic blood pressure values of 53 patients showed that:
34% had a significant reduction (t: −9.220; p<0.000);
47.2% experienced no change; and
18.9% had a significant increase (t: 5.511; p<0.000).

Results After the Second Administration of Flumazenil

The CIWA-A scoring of 58 patients showed that:
36.2% had a significant reduction (t: −5.363; p<0.000);
55.2% experienced no change; and
8.6% had a significant increase (t: 4.000; p<0.016).
The heart rate values of 55 patients showed that:
41.8% had a significant reduction (t: −8.523; p<0.000); and
58.2% experienced no change.
The systolic blood pressure values of 56 patients showed that:
28.6 had a significant reduction (t: −7.596; p<0.000);
55.4% experienced no change; and
16.1% had a significant increase (t: 4.612; p<0.002).
The diastolic blood pressure values of 56 patients showed that:
28.6% had a significant reduction (t: −6.325; p<0.000);
51.8% experienced no change (n=29); and
19.6% had a significant increase (t: 6.640; p<0.000).

Table 3 statistically summarizes the results obtained before and after the treatment (at the end of 18 hours).

TABLE 3

Statistical summary of the results obtained before and after the treatment (at the end of 18 hours)

| | X | | N EM Sig. | SD T |
|---|---|---|---|---|
| CIWA-A | | 4.13 | | 54 |
| Before treatment | | 4.28 | 0.58 | |
| | | | 6.190 | |
| | | | 0.002 | |
| CIWA-A | | 0.76 | | 54 |
| After treatment | | 1.52 | 0.21 | |
| Systolic blood pressure | 135.20 | | 51 | |
| Before treatment | 18.22 | | 2.55 | |
| | | | 5.256 | |
| | | | 0.000 | |
| Systolic blood pressure | 126.67 | | 51 | |
| After treatment | 13.99 | | 1.96 | |
| Diastolic blood pressure | 86.27 | | 51 | 10.76 |
| Before treatment | | 1.51 | | |
| | | | 3.273 | |
| | | | 0.002 | |
| Diastolic blood pressure | 82.75 | | 51 | 9.13 |
| After treatment | | 1.28 | | |
| Heart rate | 81.42 | | 53 | 13.83 |
| Before treatment | | 1.90 | | |
| | | | | 4.273 |
| | | | | 0.000 |

TABLE 3-continued

Statistical summary of the results
obtained before and after the treatment (at the end of 18 hours)

|  | X | N EM Sig. | SD T |
|---|---|---|---|
| Heart rate After treatment | 75.02 1.36 | 53 | 9.93 |

[X: Mean;
N: Number of samples;
SD: Standard deviation
EM: Mean error;
T: Student's t factor;
Sig.: Significance]

Table 4 summarizes the follow-up data.

TABLE 4

Summary of Follow-up

|  |  | Month 1 | Month 3 | Month 6 | Month 9 |
|---|---|---|---|---|---|
|  | (%/n) | 67.2/43 | 34.4/22 | 18.8/12 | 12.5/8 |
| Therapy and Disulfiram |  | 95.3% | 86.4% | 75.0% | 75.0% |
| Therapy without Disulfiram |  |  | 12.5% | 4.5% |  |
| Dropouts |  | 4.7% | 9.1% | 25.0% | 12.5% |

The psychophysiological functions such as appetite and sleep were regained very rapidly during hospitalization.

The second day of hospitalization, the patients were permitted to spend a few hours outside the clinic during the afternoon. Some patients had dinner outside the clinic.

Probably, the most striking result is the spontaneous verbal report from the majority of the patients concerning the absence of anxiety and of the desire to drink alcohol.

The invention claimed is:

1. A method to reduce a desire to drink alcohol in a patient having the desire to drink alcohol comprising administering an effective amount of flumazenil to the patient, wherein the flumazenil is administered sequentially in doses between about 0.1 and 0.3 mg of flumazenil at time intervals between about 1 and 15 minutes, wherein the amount of flumazenil is effective to reduce the desire to drink alcohol in the patient, and the effective amount of flumazenil is between about 1.5 and 2.5 mg/day.

2. The method of claim 1, wherein the amount of flumazenil that is administered in each sequential administration is about 0.2 mg.

3. The method of claim 1, wherein the flumazenil is administered at intervals of about 3 minutes.

4. The method of claim 1, wherein the effective amount of flumazenil is about 2 mg/day.

5. The method of claim 1, wherein the flumazenil is administered orally or parenterally.

6. The method of claim 5, wherein the parenteral administration of flumazenil is intravenous administration.

7. The method of claim 1, wherein the flumazenil is administered at doses of about 0.2 mg of flumazenil at intervals of about 3 minutes until an effective amount of flumazenil has been administered.

8. The method of claim 7, wherein the effective amount is about 2 mg/day.

9. The method of claim 1, wherein the flumazenil is administered before, during or after treatment with an additional agent.

10. The method of claim 9, wherein the additional agent is selected from the group consisting of Vitamin B complex, vitamins, minerals, proteins, amino acids, fluoxetine, and combinations thereof.

11. The method of claim 1, wherein the flumazenil is administered under sedation.

* * * * *

UNITED STATES PATENT AND TRADEMARK OFFICE
CERTIFICATE OF CORRECTION

PATENT NO. : 7,348,321 B2 Page 1 of 1
APPLICATION NO. : 10/621229
DATED : March 25, 2008
INVENTOR(S) : Juan Jose Legarda Ibañez It is certified that error appears in the above-identified patent and that said Letters Patent is hereby corrected as shown below:

On Title Page Item (65)

Insert under 'Domestic Priority data'

This application is a CON of PCT/ES02/00008 filed 01/10/2002

On Title Page Item (30)

Insert under 'Foreign Applications'

SPAIN P 200100106 filed 01/17/01

Signed and Sealed this

Twenty-second Day of July, 2008

JON W. DUDAS
*Director of the United States Patent and Trademark Office*